United States Patent
Hirshberg et al.

(10) Patent No.: US 6,793,787 B1
(45) Date of Patent: Sep. 21, 2004

(54) ION-SELECTIVE ELECTRODE

(75) Inventors: Moshe Hirshberg, Brookline, MA (US); Steven J. West, Hull, MA (US); James Barbookles, Ipswich, MA (US)

(73) Assignee: Orion Research, Inc., Beverly, MA (US)

( * ) Notice: Subject to any disclaimer, the term of this patent is extended or adjusted under 35 U.S.C. 154(b) by 0 days.

(21) Appl. No.: 10/098,687

(22) Filed: Mar. 15, 2002

(51) Int. Cl.⁷ ................. G01N 27/333; G01N 27/36
(52) U.S. Cl. ........................... 204/416; 204/420
(58) Field of Search ..................... 204/435, 416, 204/418, 419, 420, 417, 433

(56) References Cited

U.S. PATENT DOCUMENTS

| | | | |
|---|---|---|---|
| 2,311,977 A | * | 2/1943 | Coleman |
| 2,684,938 A | * | 7/1954 | Mantzell |
| 2,697,070 A | * | 12/1954 | Arthur |
| 3,429,785 A | | 2/1969 | Ross |
| 3,607,700 A | | 9/1971 | Tosteson |
| 3,657,093 A | | 4/1972 | Farren |
| 3,676,319 A | * | 7/1972 | Kirsten |
| 3,708,411 A | | 1/1973 | Vanslette |
| 3,894,917 A | | 7/1975 | Riseman et al. |
| 3,923,608 A | | 12/1975 | Frant et al. |
| 4,049,382 A | | 9/1977 | Ross, Jr. et al. |
| 4,052,285 A | | 10/1977 | Dobson |
| 4,059,499 A | | 11/1977 | Ibsen Nielsen et al. |
| 4,105,525 A | | 8/1978 | Synnott et al. |
| 4,166,021 A | | 8/1979 | Ross, Jr. et al. |
| 4,211,623 A | | 7/1980 | Ross, Jr. et al. |
| 4,263,104 A | | 4/1981 | Diggens et al. |
| 4,600,494 A | | 7/1986 | Bromberg et al. |
| 4,672,042 A | | 6/1987 | Ross, Jr. et al. |
| 5,490,916 A | | 2/1996 | Hall |

* cited by examiner

Primary Examiner—Alex Noguerola
(74) Attorney, Agent, or Firm—Cesari and McKenna, LLP

(57) ABSTRACT

An improved ion-selective electrode with enhanced sensitivity and reliability. The electrode is readily formed from an electrode assembly sealingly joined to the upper end of an electrode chamber whose lower end opens into in a tube bore of substantial path length that provides a conductive path between the electrode assembly and a sensing tip of the electrode. The electrode assembly itself takes the form of a generally helical coil formed on a post extending from the upper end of the assembly and positioning a substantial length of conductive lead remote from the sensing tip of the electrode. The electrode chamber is thermally insulated from the main body of the electrode, and adverse temperature effects are thus greatly minimized. A self-cleaning junction has also been developed. Increased reliability for a given sensitivity have been found to result from the construction.

16 Claims, 2 Drawing Sheets

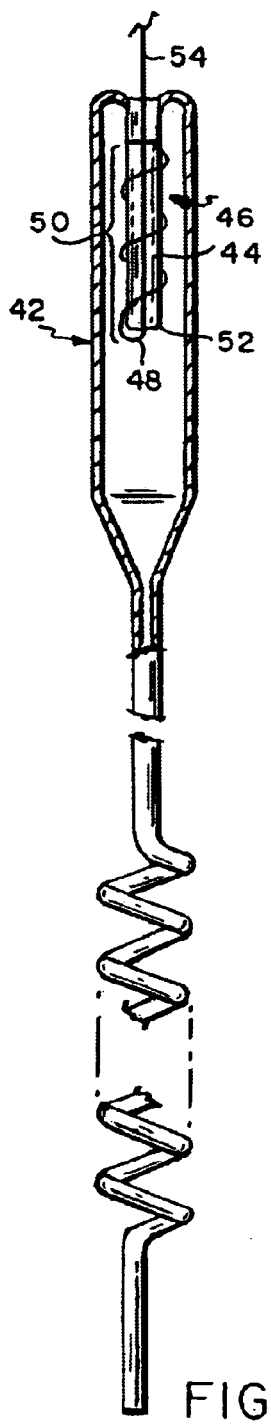
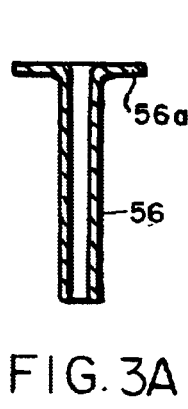
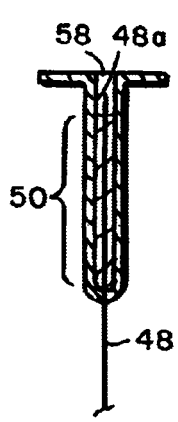
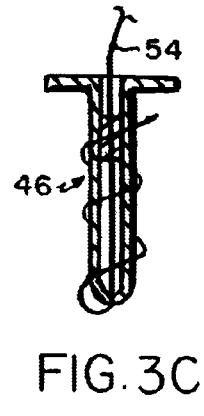
FIG. 3A  FIG. 3B  FIG. 3C
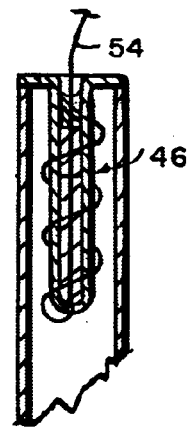
FIG. 3D
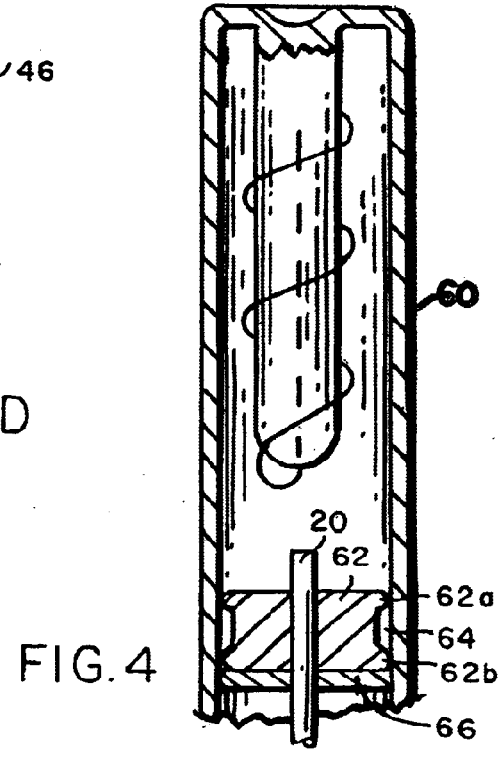
FIG. 2  FIG. 4

ION-SELECTIVE ELECTRODE

BACKGROUND OF THE INVENTION

1. Field of the Invention

The invention relates to ion-selective electrodes and comprises an improved pH electrode.

2. Background Information

Various types of ion-selective electrodes are commonly used to sense ions in solution. One such type is the pH electrode, which senses the concentration of hydrogen ions in solution. An especially important example of such electrodes is the Ross™ pH electrode, manufactured and sold by Thermo Orion, Inc.

Among the key characteristics of ion-selective electrodes are their sensitivity, accuracy and reliability. Sensitivity refers to the ability of the electrode to detect low levels of ion in solution. Accuracy refers to the correctness of the resultant reading. Reliability refers to the ability of the electrode to maintain its characteristics over extended periods of time.

Ion-selective electrodes (commonly referred to simply as "ISEs") typically contain chemical solutions of various types (referred to hereinafter as "electrolyte solutions" or "electrolyte"), both in order to provide specific characteristics to the electrode, as well as to enable electrical contact with the solution containing the ion to be measured ("the test solution"). As a result of such contact, however, the electrolyte solutions become contaminated in the course of time, and the reliability of the ISE degenerates.

SUMMARY OF THE INVENTION

Accordingly, it is an object of the present invention to provide an improved ion-selective electrode.

Further, it is an object of the invention to provide an improved ion-selective electrode of the pH type.

Still a further object of the invention is to provide an improved ion-selective electrode that is characterized by extended reliability.

Still a further object of the invention is to provide improved methods for reliably manufacturing ion-selective electrodes.

In accordance with the present invention, an improved ion-selective electrode is characterized by a substantially increased reliability for a given sensitivity. In the preferred embodiment of the invention which is described herein, the invention is specifically described as applied to a combination electrode that is manufactured and sold by Thermo Orion Corporation as a "Ross™" pH electrode, although it will be understood that the invention is not so limited and one or more aspects thereof can be expected to be applicable generally to ion-specific electrodes.

In the Ross™ pH electrode, a reference half cell body in the form of a narrow helical tube (e.g., from 1 to 2 mm. internal diameter) and filled with a first internal electrolyte solution (e.g., an iodide-triiodide solution) is contained within a larger outer body filled with an internal filling solution that provides a conductive path to the test solution (e.g., potassium chloride). The reference half cell body has upper and lower generally straight segments, and an intermediate helically-formed section. A first conductive lead (e.g., of platinum or the like) extends along the body on the interior thereof, and provides a first electrode for connection into a measuring circuit. A measuring half cell having a body in the form of a generally straight tube is also positioned within the outer enlarged body, and provides a path that connects to a bulbous tip of an ion-selective glass; the glass is sensitive to $H_+$ ion concentration and enables measurement of the pH of the test solution. A second conductive lead extends along the measuring half cell body on the interior thereof, and provides a second electrode for connection into a measuring circuit.

The pH electrode so far described has proven to be very stable over long periods of use. However, we have found that we have been able to further increase its stability for a given sensitivity, and it is to that enhancement that this invention is directed. Additionally, we have also discovered improved methods of forming conductive interfaces in ion-selective electrodes, and these also are described herein.

In particular, in accordance with the present invention, unlike prior Ross™ pH electrodes, the conductive lead of the reference half cell is removed from the vicinity of the helical coil to a position adjacent the remote end of the cell (i.e., the upper end, distant from the tip which is immersed in the test solution). In particular, the conductive lead itself is looped, preferably coiled, and is positioned within an enlarged chamber at the remote end of the half cell; the chamber is at a location above the immersion level of the electrode in the measuring fluid.

Preferably, the lead coil is itself mounted on, and preferably wound around, a post within the chamber. This construction provides a number of advantages. First, it stably positions the conductive lead of the reference electrode at a location that is most remote from the measuring tip at the sensing end of the electrode, and thus better isolates it from the contaminants that travel backwardly from the sensing end of the electrode to the reference electrode lead. The isolation arises both from the increased path length between the frontal terminus of the inner electrolyte path through which contaiminantions may flow backwardly into the reference half cell body and thence back up to the reference lead itself, and also from the thermal isolation arising from placing the reference lead in a chamber that is both of substantially larger cross-section than the reference body (and thus of substantially greater thermal inertia) and that is also maintained at a location removed from contact with that portion of the electrode that is immersed. Thus, thermal transfer from the test solution to the reference lead is minimized.

Additionally, the construction enables a substantial length of conductive wire to be placed in contact with the reference electrolyte, while yet maintaining an increased separation from the sensing tip. This contributes to an enhanced lifetime for the overall electrode. For example, we have found that by providing a reference lead of length of about 25 mm. of 0.25 diameter and formed in a coil or an otherwise folded configuration, the lifetime of the electrode is significantly increased as compared to a construction in which the reference lead extends essentially axially along the conductive path. Despite its length, however, the entire surface of the electrode is still positioned more remotely from the measuring tip, thus providing the desirable electrical and thermal benefits. In effect, the construction enables the use of an increased length of conductive lead in the reference electrode without concurrently increasing the susceptibility of the electrode to interfering ions from the solution.

As indicated above, the reference half cell construction is accompanied by enlargement of the upper end of the reference body into a chamber of substantially greater cross section, and thus volume per unit length, than the main body of the tube to which it connects For example, in one implementation we have constructed a chamber having an internal diameter of approximately 6-8 millimeters, and a length of approximately 35–40 millimeters, resulting in a volume of 200–300 mm$^3$. The lower end of the chamber communicated with the remainder of the reference body in the form of a narrow tube of approximately 1–2 millimeters, and providing a total volume at least several times less than that of the chamber. The reference lead was sealed to the upper end of the chamber. The chamber was further thermally isolated from the sensing tip by enclosing it in a separate housing thermally insulated from the main body of the electrode. In the particular implementation described here, the thermal isolation was provided by gaskets of low thermal conductivity interposed between the main body and the chamber housing. This construction was found to significantly extend the lifetime of electrodes.

A further aspect of the present invention resides in the structure of the interface end of the reference electrolyte body. The interface end is that end at which contact with the internal filling solution is made. Heretofore, the interface has typically been formed by means of a ceramic plug positioned within the body and extending a short distance along the body from its end. The plug provides a path along which ions may migrate from the internal filling solution into the reference filling solution, and thus to the reference lead. Although this structure is acceptable, we believe that the construction of the electrode will be further facilitated by the structure and process we now describe.

Specifically, we have found that an effective interface may be formed by sealing off the lower end of the reference half cell body into which the ceramic plug is usually inserted and instead forming a bore through a portion of the body at the lower end. Either before or after this is done, the outer face of the body surrounding the bore hole is abraded by sand blasting or the like. A sleeve of tubing is then snugly fitted over the abraded area For reasons which will become clear shortly, the tubing and the sleeve are selected such as to have different coefficients of thermal expansion. We have found that a reference body of glass (whether lead, Pyrex, or other) and a sleeve of a plastic, preferably a fluorocarbon, such as Teflon, provides the requisite differential thermal coefficients.

The resultant construction provides an ion-conductive path between the outside wall of the reference body and the sleeve and thence through the bore hole and into the interior of the reference body, while preventing the discharge of reference electrolyte from the body. It thus serves the same function as the ceramic plug. However, it has a number of advantages over the prior construction. First, it enables rapid filling of the reference tube through the bore hole. Second, it enables cleaning of the reference interface. In particular, over time, some of the internal filling solution in which the reference half cell is placed crystallizes and blocks the ion-conductive path into the reference body. When this occurs with a ceramic plug, it is difficult, if not impossible, to clean the plug in situ; thus the plug must be removed and the reference half cell reconstructed with a new plug. With the structure of the present invention, however, the half cell is cleaned whenever the temperature of the electrolyte in the vicinity of the bore and sleeve is changed. This occurs most commonly when the electrode is immersed in a test solution for measurement. Due to the differences in coefficients of thermal expansion, a gap will form between the reference body and the sleeve and cleansing fluid can flow into this gap to thereby clean it of accumulated crystallized electrolyte or other contaminants that may have accumulated between the sleeve and the body. Thus, the structure is self-cleaning.

We also describe various techniques for conveniently forming the new pH electrode described herein. In one embodiment, the helical tube is formed by starting with a glass tube of substantially larger cross section than the desired tube and drawing one end of the tube in a flame or other heat source in known manner in order to form an extended tube at one end thereof, and an enlarged electrode chamber at the other end. The extended tube portion is then formed into a helix while under heat. Thus, a continuous reference electrode structure having a tube coil feeding into an enlarged electrode chamber is thereby formed. In another embodiment, the electrode chamber is formed separately from the helical coil, and the two are joined through a gasket press-fitted into the chamber at the distal end thereof. In one such embodiment, the gasket is a cylindrical plug. In another, the gasket has a midsection of reduced diameter to thereby form upper and lower ribs which separately contact the interior of the chamber wall to provide a tighter seal therewith.

In both of the embodiments described above, the reference half cell is preferably fitted to the lead chamber by means of a preform that is placed against the remote end (i.e., the top) of the lead chamber and sealed thereto. Advantageously, the preform is in the form of a glass tube having an elongated cylindrical body. An upper end of the tube is flared to facilitate joinder to the electrode chamber. A wire comprising the reference lead is placed within the tube at a location somewhat below the flared end, and extending outwardly from the other end of the tube for a distance of about 25 millimeters. The lower portion of the tube is then fired under heat sufficient to melt the glass tube and to bond the wire within such portion to form a fluid-tight seal between the tube and the electrode lead. This also creates a well in the upper part of the tube into which an upper portion of the electrode lead wire extends. This will facilitate subsequent electrical connection thereto as will shortly be described. That portion of the lead wire extending outwardly of the tube is then wrapped around the around the exterior of the tube in a generally helical pattern to complete the desired preform. The preform is thereafter securely fitted to the upper end of the lead chamber, such as by bonding to it, to form a fluid-tight seal. Finally, an external lead is bonded to the preform electrode lead by filling the well, or a portion of it, with an electrically-conductive sealant (e.g., melted platinum) to complete the electrode construction.

Although the invention herein is not so restricted, preferably the lead chamber, half cell body, and preform are made of glass and the sealing is done by means of glass-glass and/or glass-metal seals to form fluid tight seals by techniques well known to those involved in the manufacture of glass ion-selective electrodes.

BRIEF DESCRIPTION OF THE DRAWINGS

The invention description below refers to the accompanying drawings, of which:

FIG. 2 is a vertical sectional view of the upper end of the electrode of FIG. 1, showing the construction of the electrode chamber in more detail;

FIGS. 3A–3D are vertical sectional views illustrating the formation of the electrode preform in detail;

FIG. 4 is a vertical sectional view an alternative form of the electrode of FIG. 1.

DETAILED DESCRIPTION OF AN ILLUSTRATIVE EMBODIMENT

Figure 1:
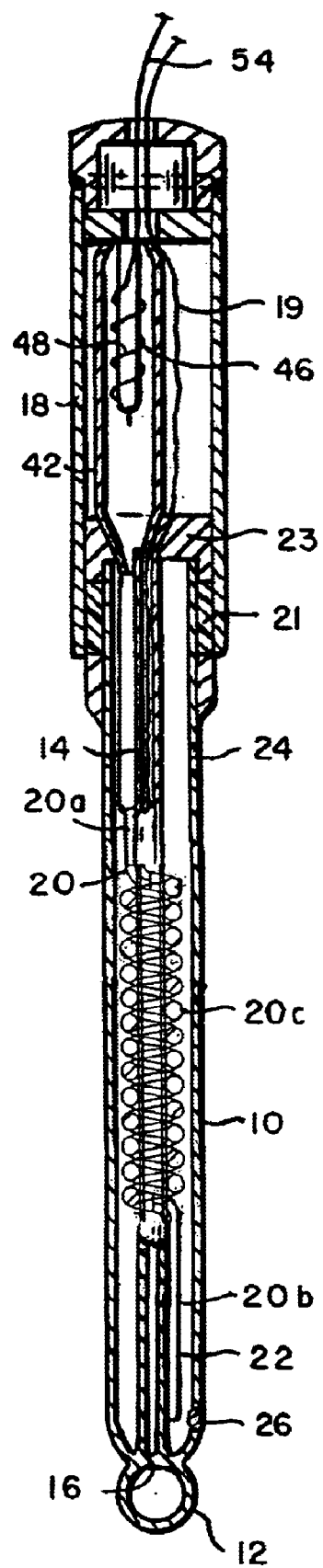
FIG. 1 is a view in perspective of a preferred form of an improved ion-selective electrode in accordance with the present invention.

In FIG. 1, an ion-selective electrode in the form of a combination pH electrode illustrating the present invention is shown. The particular form of electrode shown here is of a type known generally as a Ross™ pH electrode, manufactured and sold by Thermo Orion, Inc., modified, however, to incorporate the present invention. The electrode of FIG. 1 has a generally cylindrical body 10 of glass or other suitable material, terminating in a bulb 12 of pH sensitive glass. A tube 14 centrally disposed in the body 10 connects to the bulb 12 through a porous wall 16; the tube extends upwardly from bulb 12 toward the top of the electrode. A sensing electrolyte (not shown) fills bulb 12 and tube 14 and provides an electrically-conductive path between a liquid (not shown) in which bulb 12 may be immersed and an electrically conductive lead 19 disposed within the electrolyte and extending upwardly and out through the top of the electrode 10 to a measuring instrument (not shown). The bulb 12, tube 14, and electrode form a half-cell pH sensing electrode in known manner.

A reference half-cell also contained within body 10 has a narrow tube 20 that in part encompasses the tube 14. The tube has upper, 20a, and lower, 20b, straight tube sections and an intermediate tube coil section, 20c. The lower section 20b is stoppered by a porous ceramic plug 22. An electrolyte solution (not shown) fills the tube.

A bore 24 extends through the wall of body 10 in order to provide a port through which an electrolyte filling solution (not shown) may be injected. The filling solution extends up to a level that completely immerses the lower end of the ceramic plug 22, and typically extends to a point a little below the level of the port 24. A porous ceramic frit 26 formed in the wall of body 10 provides a conductive path through which ions from a test solution in which the body 10 is immersed can travel into the filling solution, and thence through the porous plug 22 into the electrolyte solution in coil 22 and thence upwardly through the coil.

So far the construction described is generally that of the previously-known Ross pH electrode and does not comprise our invention. The modification to that electrode which does comprise our invention will now be described.

In particular, the tube 20 extends into, and terminates in, an enlarged electrode chamber 42 in an upper housing 18. The housing 18 is attached to the body 10 by means of a thermally-insulating gasket 21 of rubber, plastic, or the like, and layer of epoxy 23 may be used fix the chamber 42 securely in place. The chamber 42 is generally of the form of an elongated cylinder 43 (see FIG. 3D) having an electrode assembly 46 sealed to the topmost portion thereof and extending downwardly therefrom. The electrode assembly is shown in more detail in FIGS. 2 and 3, and comprises a central post 44 and an electrically conductive lead 48 extending through a central core on the interior of the post and internally bonded within the post throughout at least a region 50 to form a fluid-tight seal therewith. On emerging from the bottom 52 of the post 44, the lead 48 is coiled back around the exterior of the post in a generally helical configuration. The stiffness of the lead is preferably sufficiently great that the coil remains essentially fixed in place without the need for adhesives or other bonding to the post. An electrically conductive lead 54 is conductively connected to the lead 48 at the upper end of the chamber 42 as will subsequently be described in more detail. The lead 54 connects to an external measuring instrument (not shown).

Referring more specifically to FIGS. 3A–D, a more detailed description of a preferred form of construction of the electrode chamber will now be given. The electrode assembly for the chamber advantageously starts as a cylindrical tube 56 whose upper end 56a is flared to facilitate attachment to the electrode chamber 42. An electrically conductive lead 48, of substantially greater length than the tube 54, is inserted into the tube 56, with the upper end of the lead located somewhat below the top of the tube, as shown in FIG. 3B, and the lower end extending outwardly from the tube. The upper end of lead 48 preferably has a crook 48a or may be coiled or looped for reasons which will become clear hereinafter. A lower portion 52 of the tube 56 is then sealed in order to form a fluid-tight bond between the tube and the lead 48 on the interior of the tube. For example, when the tube is of glass, the seal is readily accomplished by heating the lower portion of the tube until the glass starts to melt and to reform itself about the lead 48. In the process of subsequently cooling, the lower portion of the tube shrinks inwardly around the lead to form the solid post 44 in which electrode lead 48 is now embedded. This process leaves a well 58 in the upper end of tube 44 into which the upper end 48a of lead 48 extends. That portion of lead 48 extending downwardly and exteriorly of post 44 is then coiled around the post on the exterior thereof to complete construction of the electrode assembly 46 (see FIG. 3C).

As shown in FIG. 3D, the assembly 46 is next fluid-tight bonded to the upper face of electrode chamber housing 42; prior to this, the upper end of the chamber is open. Conductive lead 54 is then bonded to the electrode assembly for connecting it to external circuitry (not shown). This is preferably accomplished simply by melting a conductive material such as platinum into the well 58 (see FIG. 3C) of electrode assembly 44 and thereafter inserting the lead 54 into the well. On cooling, the molten material solidifies into a mass 60 that encompasses the exposed portion 48a of lead 48 and thereby provides a low-resistance electrical connection to lead 54.

Rather than form the electrode chamber 42 integral with the tube section 20 as so far described, the two may be formed separately and thereafter interconnected. A preferred embodiment of such a construction is shown in FIG. 4, in which an electrode chamber 60, preferably generally cylindrical, having an electrode assembly 46 in the up per end thereof has a gasket 62 near the lower end thereof through which the upper end of tube 20 extends. The gasket 62 preferably has upper 62a and lower 62b lips creating a cavity 64 with the interior wall of chamber 60. This enables a firm fit of the gasket 62 within the housing of chamber 60 and facilitates a liquid-tight seal. A layer of sealant 66 may additionally secure the lower end of the assembly in a fluid-tight manner.

Figure 5:
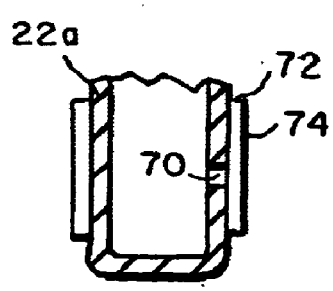
FIG. 5 is a sectional view of an improved interface structure in accordance with the present invention.
Figure 5A:
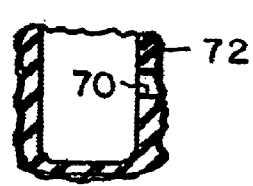

FIG. 5 shows an alternative construction for the reference half cell interface at the lower end of body 20b (see FIG. 1). This construction eliminates the need for the porous plug 22. In particular, in this alternative, the lower end of body 22 is closed, as shown in FIG. 5, and a bore 70 is formed through the wall of the body. The area surrounding the bore is abraded to form a pitted or roughened microsurface surface 72 as shown illustratively at 74 in FIG. 5A. This is preferably done simply by sandblasting the area. A sleeve 74, having a coefficient of thermal expansion that is different than that of the body 22, is then fitted over this surface to form a snug fit with respect thereto. Because of the pitted surface of the body, an ion-conductive path or channel is thereby formed between the outer body wall and the inner face of the sleeve. Whenever the electrode is immersed in a heated fluid, the sleeve expands more than the body and enlarges the cross-section of the channel. It also allows a small amount of reference electrolyte to flow outwardly from the body 22, and this cleans the path of contaminants that may have accumulated. Conversely, when the electrode is removed from the heated liquid and returns to its equilibrium temperature, the reverse process takes place: the sleeve shrinks more tightly onto the body 22. At the same time, a small amount of filling solution is drawn into the body 22, cleaning the path between the body 22 and the sleeve 74 as it does so. Thus, the interface is self-cleaning, and this contributes to enhancement the electrode lifetime. We have found that heating the electrode by about 15 degrees centigrade and thereafter allowing it to cool reliably cleans the interface or junction.

From the foregoing, it will be seen that we have provided an improved ion-selective electrode with enhanced sensitivity and reliability. The electrode is readily formed from an electrode assembly sealingly joined to the upper end of an electrode chamber whose lower end opens into in a tube bore of substantial path length that provides a conductive path between the electrode assembly and a sensing tip of the electrode. The electrode assembly itself takes the form of a generally helical coil formed on a post extending from the upper end of the assembly and positioning a substantial length of conductive lead remote from the sensing tip of the electrode. The electrode chamber is thermally insulated from the sensing tip which is immersed in liquids of varying temperatures, thus diminishing the effects of such temperatures on the measurements. Increased reliability for a given sensitivity have been found to result from the construction.

What is claimed is:

1. An improved ion-selective electrode, comprising:
  A. a sensing tip at one end thereof and an electrode chamber at another end thereof remote from said tip,
  B. an electrode assembly including a post having first and second ends and an interior conductive lead extending through said post on the interior thereof and in fluid-tight engagement therewith along a portion thereof, said lead continuing exteriorly of said post at said second end and formed into a generally helical coil surrounding said post, said electrode chamber enclosing said post therein and joined in fluid-tight engagement at a first end of said chamber to a first end of said post, and
  C. a tube connected to a second end of said chamber and extending toward said sensing tip, for providing an electrically-conductive path from said tip to said lead.

2. An improved ion-selective electrode according to claim 1 in which said first end of said post opens into a well into which a first end of said conductive lead extends, said well communicating with the exterior of said electrode chamber.

3. An improved ion-selective electrode according to claim 2 which includes an exterior lead in electrical contact with at least a portion of said interior lead in said well.

4. An improved ion-selective electrode according to claim 3 in which said electrical contact is formed by a mass of electrically conductive material in said well.

5. An improved ion-selective electrode according to claim 1 in which said post has an outwardly flared flange formed at said first end thereof for sealing said post to said chamber.

6. An improved ion-selective electrode according to claim 1 in which said coil is formed on the exterior of said post.

7. An improved ion-selective electrode according to claim 1 in which said post is formed from a glass tube through which said conductive lead is extended and fused to said lead along said portion to form a fluid-tight glass-to-metal seal therewith.

8. An improved ion-selective electrode according to claim 7 in which the volume of said chamber is at least 4 times the volume of said tube.

9. An improved ion-selective electrode according to claim 1 in which the cross-sectional area of said chamber is at least 4 times the cross-sectional area of said tube.

10. An improved ion-selective electrode according to claim 1 in which the volume of said chamber is at least 4 times the volume of said tube.

11. An improved ion-selective electrode according to claim 1 in which said chamber is connected at said second end thereof to said tube by a section of gradually-reducing diameter.

12. An improved ion-selective electrode according to claim 1 in which said chamber is connected to said tube by means of a gasket encompassing said tube along a portion thereof and in fluid-tight engagement therewith.

13. An improved ion-selective electrode according to claim 12 in which said gasket and at least a portion of said chamber are generally cylindrical in shape, said gasket having first and second flanges thereon encompassing an intermediate necked-in region to form a fluid-light seal with said chamber.

14. An improved ion-selective electrode, comprising:
  A. a sensing tip at one end thereof and an electrode chamber at another end thereof remote from said tip, said chamber having an upper end thereof remote from said tip and a lower end closer to said tip,
  B. an electrode assembly comprising a conductive coil fixed in the interior of said chamber at said upper end and having a portion thereof extending through said upper end for connection to an external circuit, and
  C. a tube connected to the lower end of said chamber and extending toward said sensing tip, for providing an electrically-conductive path from said tip to said coil.

15. An improved ion-selective electrode according to claim 14 in which said coil is wrapped around a post.

16. An improved ion-selective electrode according to claim 15 in which said coil is of sufficiently small diameter as to be effectively fixed in place without being sealed or bonded to said post.

* * * * *